United States Patent
Sharma et al.

(10) Patent No.: US 7,189,755 B2
(45) Date of Patent: Mar. 13, 2007

(54) PYRROLIDINE MELANOCORTIN-SPECIFIC COMPOUNDS

(75) Inventors: Shubh D. Sharma, Cranbury, NJ (US); Yi-Qun Shi, East Brunswick, NJ (US); Zhijun Wu, Plainsboro, NJ (US); Ramesh Rajpurohit, Hillsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 435 days.

(21) Appl. No.: 10/776,657

(22) Filed: Feb. 10, 2004

(65) Prior Publication Data

US 2004/0167201 A1  Aug. 26, 2004

Related U.S. Application Data

(63) Continuation-in-part of application No. PCT/US02/25574, filed on Aug. 12, 2002.

(60) Provisional application No. 60/311,404, filed on Aug. 10, 2001.

(51) Int. Cl.
A61K 31/4025 (2006.01)
C07D 207/04 (2006.01)

(52) U.S. Cl. ............ 514/423; 544/224; 544/242; 544/297; 546/268.1; 546/276.4; 546/277.7; 548/125; 548/136; 548/262.2; 548/300.1; 548/311.1; 548/364.1; 548/530; 548/537; 514/275; 514/336; 514/340; 514/424

(58) Field of Classification Search .......... 548/125, 548/136, 537, 300.1, 311.1, 314.7, 364.1; 544/242, 297; 546/268.1, 277.7; 514/256, 514/336, 423, 424
See application file for complete search history.

(56) References Cited

U.S. PATENT DOCUMENTS

| | | | |
|---|---|---|---|
| 4,148,923 A | 4/1979 | Guidicelli et al. |
| 4,239,763 A | 12/1980 | Milavec et al. |
| 4,626,549 A | 12/1986 | Molly et al. |
| 4,680,289 A | 7/1987 | Applezweig |
| 4,937,267 A | 6/1990 | Holloway et al. |
| 5,120,713 A | 6/1992 | Mugica |
| 5,494,919 A | 2/1996 | Morriello et al. |
| 5,721,250 A | 2/1998 | Morriello et al. |
| 5,721,251 A | 2/1998 | Chen et al. |
| 5,804,578 A | 9/1998 | Chakravarty et al. |
| 5,877,182 A | 3/1999 | Nargund et al. |
| 5,880,125 A | 3/1999 | Nargund |
| 5,965,565 A | 10/1999 | Chen et al. |
| 6,033,656 A | 3/2000 | Mikami et al. |
| 6,127,424 A | 10/2000 | Martin et al. |
| 6,140,354 A | 10/2000 | Dax et al. |
| 6,162,805 A | 12/2000 | Hefti |
| 6,191,117 B1 | 2/2001 | Kozachuk |
| 6,207,699 B1 | 3/2001 | Rothman |
| 6,214,831 B1 | 4/2001 | Yokoo et al. |
| 6,284,735 B1 | 9/2001 | Girten et al. |
| 6,350,760 B1 | 2/2002 | Bakshi et al. |
| 6,376,509 B1 | 4/2002 | Bakshi et al. |
| 6,410,548 B2 | 6/2002 | Nargund et al. |
| 6,451,783 B1 | 9/2002 | Hadcock et al. |
| 6,458,790 B2 | 10/2002 | Palucki et al. |
| 6,472,398 B1 | 10/2002 | Palucki et al. |
| 6,515,122 B1 | 2/2003 | Lang et al. |
| 6,534,503 B1 | 3/2003 | Dines et al. |
| 6,579,968 B1 | 6/2003 | Blood et al. |
| 2002/0004512 A1 | 1/2002 | Bakshi et al. |
| 2002/0072604 A1 | 6/2002 | Carpino et al. |
| 2002/0137664 A1 | 9/2002 | Bakshi et al. |

(Continued)

FOREIGN PATENT DOCUMENTS

WO    WO 96/38471    12/1996

(Continued)

OTHER PUBLICATIONS

"Synthetic Peptides: A Users Guide," GA Grant, editor, W.H. Freeman & Co., New York, 1992 (pp. 11-24).

(Continued)

Primary Examiner—Golam M. M. Shameem
(74) Attorney, Agent, or Firm—Stephen A. Slusher

(57) ABSTRACT

Melanocortin receptor-specific pyrrolidine compounds having the structure:

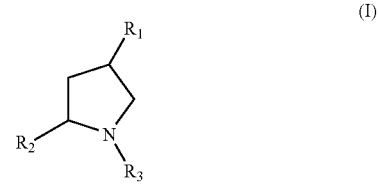

(I)

and stereoisomer and pharmaceutically acceptable salts thereof, where $R_1$, $R_2$, and $R_3$ are as described in the specification, preferably where $R_3$ is a D-amino acid with at least one substituted or unsubstituted phenyl or naphthyl aromatic ring, and where $R_3$ optionally further includes an amine capping group or from one to three additional amino acid residues, optionally with an amine capping group, which compounds are agonists, antagonists or mixed agonists and antagonists at one or more melanocortin receptors, and having utility in the treatment of melanocortin receptor-related disorders and conditions. Methods of synthesis of compounds of structure (I), pharmaceutical compositions containing a compound of structure (I) and methods relating to the use thereof are also disclosed.

12 Claims, No Drawings

U.S. PATENT DOCUMENTS

| | | |
|---|---|---|
| 2002/0143141 A1 | 10/2002 | Chen et al. |
| 2002/0173512 A1 | 11/2002 | Moltzen et al. |
| 2003/0004162 A1 | 1/2003 | Treadway |
| 2003/0055247 A1 | 3/2003 | Cosford et al. |
| 2003/0055265 A1 | 3/2003 | Binggeli et al. |
| 2003/0069169 A1 | 4/2003 | Macor et al. |
| 2003/0083228 A1 | 5/2003 | Carpino et al. |
| 2003/0109556 A1 | 6/2003 | Mazur et al. |

FOREIGN PATENT DOCUMENTS

| | | |
|---|---|---|
| WO | WO 98/10653 | 3/1998 |
| WO | WO 99/58501 | 11/1999 |
| WO | WO 00/05373 | 2/2000 |
| WO | WO 00/35952 | 6/2000 |
| WO | WO 00/40247 | 7/2000 |
| WO | WO 01/12176 | 2/2001 |
| WO | WO 01/21634 | 3/2001 |
| WO | WO 01/21647 | 3/2001 |
| WO | WO 01/182210 | 3/2001 |
| WO | WO 01/23392 | 4/2001 |
| WO | WO 01/30343 | 5/2001 |
| WO | WO 01/55106 | 8/2001 |
| WO | WO 01/55107 | 8/2001 |
| WO | WO 01/55109 | 8/2001 |
| WO | WO 02/12178 | 2/2002 |
| WO | WO 02/18437 | 3/2002 |
| WO | WO 02/47670 | 6/2002 |
| WO | WO 02/059108 | 8/2002 |
| WO | WO 02/064091 | 8/2002 |
| WO | WO 02/067869 | 9/2002 |
| WO | WO 02/068387 | 9/2002 |
| WO | WO 02/079203 | 10/2002 |
| WO | WO 02/079753 | 10/2002 |
| WO | WO 03/006620 | 1/2003 |
| WO | WO 03/009847 | 2/2003 |
| WO | WO 03/013509 | 2/2003 |
| WO | WO 02/085925 | 6/2003 |
| WO | WO 03/061660 | 7/2003 |
| WO | WO 02/081443 | 10/2003 |

OTHER PUBLICATIONS

Hruby, VJ, Al-Obeidi, F., and Kazmierski, W.: BioChem Journal 268:249-262, 1990.

Toniolo, C., "Conformationally Restricted Peptides Through Sort-Range Cyclizations," International Journal Peptide Research, 35:287-300, 1990.

Hadley, M.E., et al., "Discovery and Devleopment of the Novel Melanogenic Drugs," Integration of Pharmaceutical Discovery and Development: Case Studies, Borschart, et al. editors, Plenum Press, New York (1998).

Dorr, R.T., et al., Evaluation of Melanotan-II, A Superpotent Cyclic Melanotropic Peptide in a Pilot Phase-I Clinical Study, Life Sciences 58:1777-1784 (1996).

Adan, R.A.H., "Identification of Antagonists for Melanocrotin MC3, MC4, and MC5 Receptors", European Journal Pharmacology, 269:331-337 (1994).

Merrifield, R.B., "Solid Phase Synthesis" (Nobel Lecture), Agnew Chem 24:799-810 (1985).

PYRROLIDINE MELANOCORTIN-SPECIFIC COMPOUNDS

CROSS-REFERENCE TO RELATED APPLICATIONS

This application is a continuation-in-part application of International Application No. PCT/US02/25574, International Publication No. WO 03/013571, entitled "Peptidomimetics of Biologically Active Metallopeptides", filed on Aug. 12, 2002, which claimed the benefit of the filing of U.S. Provisional Patent Application Ser. No. 60/311,404, entitled "Receptor-Specific Peptides Derived from Biologically Active Metallopeptides", filed on Aug. 10, 2001, and the specification thereof of each is incorporated herein by reference.

BACKGROUND OF THE INVENTION

1. Field of the Invention (Technical Field)

The present invention relates to pyrrolidine molecules with three biologically relevant pendant groups that bind to one or more melanocortin receptors and are agonists, antagonists or mixed agonist-antagonists.

2. Description of Related Art

Note that here and elsewhere the specification refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of tissues.

In general, compounds specific for MC1-R are believed to be useful for treatment of melanoma and melanin-associated disorders, inflammatory diseases and other conditions which may be positively affected by stimulation or down regulation of MC1-R. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and other food intake and metabolism-related purposes and disorders. Compounds specific for MC3-R and MC4-R, among other melanocortin receptors, can be used as agents for treatment of sexual dysfunction, including male erectile dysfunction. Other melanocortin receptor-specific compounds, such as MC1-R agonists, can be used as tanning agents to increase melanin production. Compounds specific for MC1-R, MC3-R and MC5-R may be useful in regulation of inflammatory processes.

WO 02/085925, "Melanocortin Receptor Ligands", to The Proctor & Gamble Company, discloses a variety of structures, including a pyrrolidine structure, but wherein certain groups thereof, and the method of synthesis, differ from those disclosed herein.

There is a significant need for compounds with high specificity for discrete melanocortin receptors, as well as compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

BRIEF SUMMARY OF THE INVENTION

In one embodiment, the invention provides a compound having the structure:

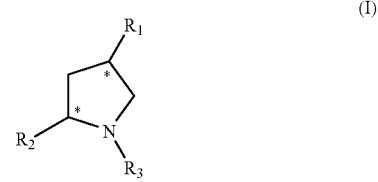

(I)

or a stereoisomer or pharmaceutically acceptable salt thereof, wherein $R_1$ is $-L_1-J$;

$R_2$ is selected from the group consisting of $-(C=O)-W$ and $-(C=O)-NH-(CH_2)_y-W$;

$R_3$ is $-L_2-Q$;

$L_1$ is a linker selected from the group consisting of $-(CH_2)_y-$, $-O-(CH_2)_y-$, $-O-$, $-NH-(CH_2)_y-$, $-(C=O)(CH_2)_y-$, $-(C=O)-O-(CH_2)_y-$, $-CH_2(C=O)NH-$, and $-(C=O)-NH-(CH_2)_y-$;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or $-O-$, and substituted or unsubstituted aromatic fused heterobicyclic ring groups; wherein in each instance the rings comprise 5 or 6 ring atoms;

W is a heteroatom unit with at least one cationic center, hydrogen bond donor or hydrogen bond acceptor wherein at least one atom is N;

$L_2$ is a linker selected from the group consisting of

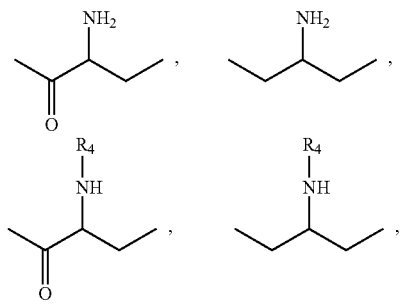

-continued

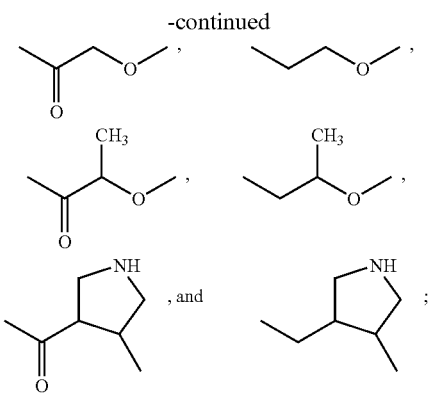

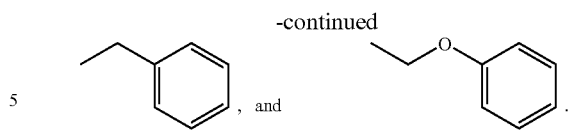

Q is an aromatic carbocyclic ring selected from the group consisting of phenyl, substituted phenyl, naphthyl and substituted naphthyl;

$R_4$ is —$R_5$ or —$R_5$—$R_6$;

$R_5$ is from one to three amino acid residues or an amine capping group, provided that if $R_6$ is present, $R_5$ is at least one amino acid residue;

$R_6$ is H or an amine capping group; and y is at each occurrence independently from 0 to 6;

wherein the carbon atoms marked with an asterisk can have any stereochemical configuration.

In the compound of structure (I), J can be a substituted or unsubstituted ring structure selected from the group consisting of

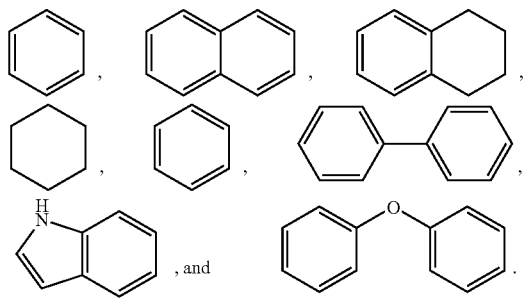

In one embodiment, the at least one ring including J is functionalized with one or more halogen, alkyl or aryl groups.

In the compound of structure (I), $R_1$ can be selected from the group consisting of

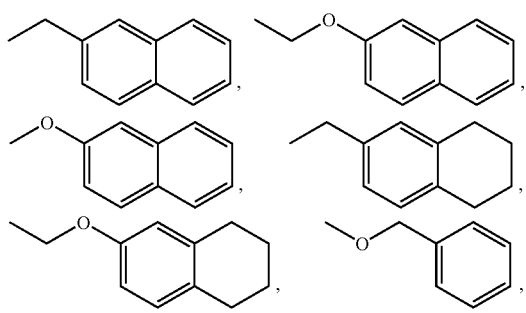

In a preferred embodiment, $R_1$ is selected from the group consisting of

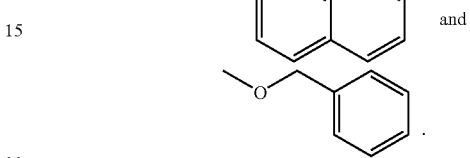

Preferably in the compound of structure (I) $R_2$ is —(C=O)—NH—$(CH_2)_y$—W, and more preferably wherein $R_2$ is selected from the group consisting of

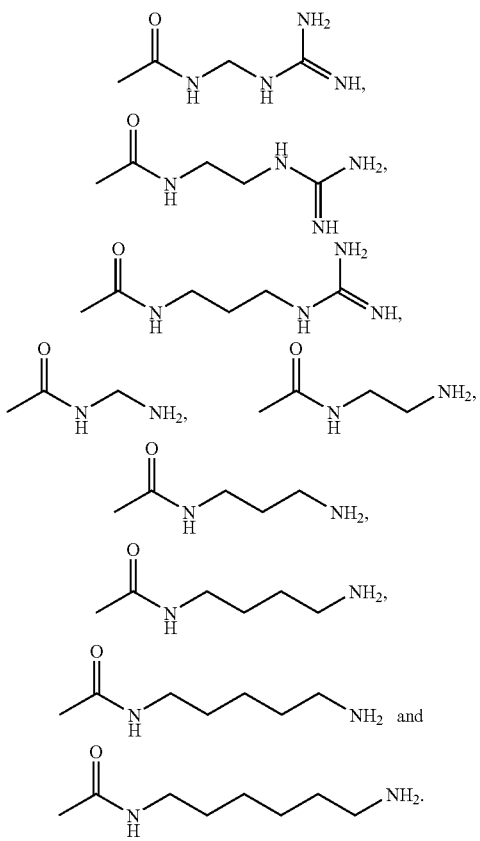

W is preferably a cationic center selected from the group consisting of $NH_2$ and $NH(C=NH)NH_2$. Alternatively, W is a heteroatom unit with at least one cationic center, hydrogen bond donor or hydrogen bond acceptor wherein at least one atom is N, preferably selected from the group consisting of —$NHCOCH_3$, —$CONHCH_3$, —$NH(C=NH)NHMe$, —$NH(C=NH)NHEt$, —$NH(C=NH)NHPr$, —NH (C=NH)NHPr—I, —NH(C=NH)NH₂, —NH(C=O)OCH₃, —NH(C=O)CH₃, NH(C=O)NH₂, —NH(C=O)NHCH₃,

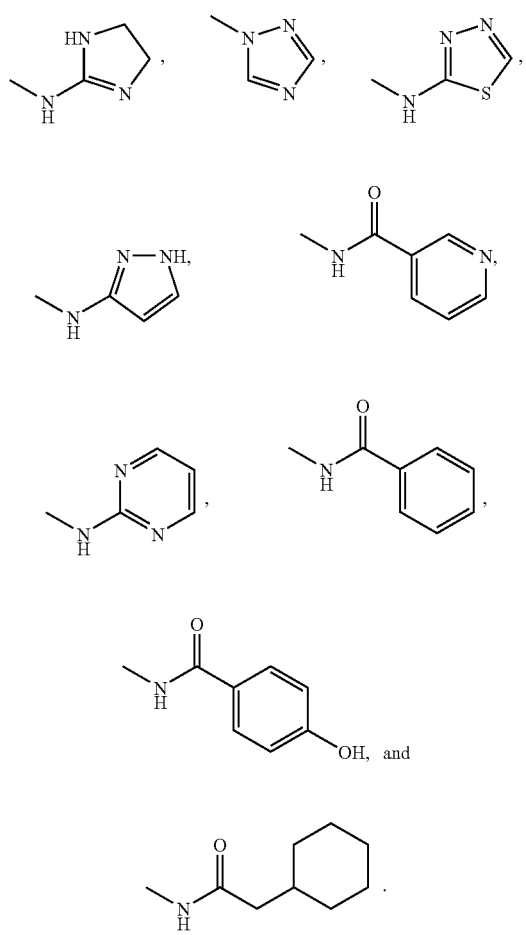

In the compound of formula (I), Q can be

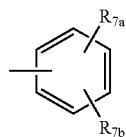

wherein R$_{7a}$ and R$_{7b}$ are optional ring substituents, and when one or both are present, are the same or different and independently hydroxyl, halogen, alkyl, or aryl groups attached directly or through an ether linkage. The alkyl group can be —CH₃ or —OCH₃.

In the compound of formula (I), either R$_5$ or R$_6$ can be an amine capping group selected from the group consisting of hexyl, hexanoyl, heptanoyl, acetyl, phenylacetyl, cyclohexylacetyl, propylpentanoyl, naphthylacetyl, cinnamoyl, benzyl, benzoyl, benzyloxycarbonyl, cinnamoyl, 12-Ado, 7'-amino heptanoyl, 6-Ahx, Amc and 8-Aoc.

In the compound of formula (I), R$_3$ can be a D-amino acid with an aromatic carbocyclic ring selected from the group consisting of phenyl, substituted phenyl, naphthyl and substituted naphthyl. R$_3$ can further be a D-amino acid with an amine capping group and an aromatic carbocyclic ring selected from the group consisting of phenyl, substituted phenyl, naphthyl and substituted naphthyl. In another embodiment, R$_3$ can be from two to four amino acid residues including a D-amino acid with an aromatic carbocyclic ring selected from the group consisting of phenyl, substituted phenyl, naphthyl and substituted naphthyl wherein the D-amino acid is bonded to the ring nitrogen. In yet another embodiment R$_3$ can be from two to four amino acid residues including a D-amino acid with an aromatic carbocyclic ring selected from the group consisting of phenyl, substituted phenyl, naphthyl and substituted naphthyl and bonded to the ring nitrogen and wherein the N-terminus amino acid residue has an amine capping group. Thus R$_3$ can include a D-amino acid selected from the group consisting of Phe, Phe(2-Cl), Phe(4-Cl), Phe(2,4-diCl), Phe(2,4-diF), Phe(3,4-diCl), Phe(4-NO₂), Phe(4-Me), Phe(4-Phenyl), HPhe, pF-Phe, Phe(4-Br), Phe(4-CF₃), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4-CF₃), and Phe(3,4-di-OMe). Alternatively, R$_3$ can include a D-amino acid is selected from the group consisting of Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Ser(p-Cl-Phenyl), Lys(Z), Lys(Z-2'Br), Lys(Bz), Thr(Bzl), Tic, Tiq, Cys(Bzl), Tyr(2,6-DiCl-Bzl) and Tyr(Bzl).

In the compound of formula (I), R$_5$ can be from one to three amino acid residues selected from the group of L-amino acids consisting of Abu, 2-Abz, 3-Abz, 4-Abz, 1-Ach, Acp, Aib, Ala, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBzA, B-Gpa, GVA(Cl), His, hSer, Ser(Bzl), Tic, hHyp, Hyp(Bzl), Inp, 2-Naphthylacetyl, Nle, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl) and Thr(O-2-Cl-Phenyl), Tyr, Leu, Ile, Val and Beta-Ala.

In another embodiment, the invention provides a compound having the structure:

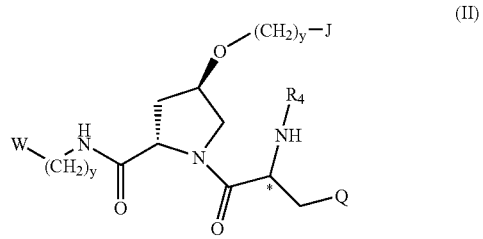

or a stereoisomer or pharmaceutically acceptable salt thereof, wherein y, J, W, Q, R$_4$, R$_5$ and R$_6$ are as defined above, and the carbon atom marked with an asterisk can have any stereochemical configuration.

In another embodiment, the invention provides a compound having the structure:

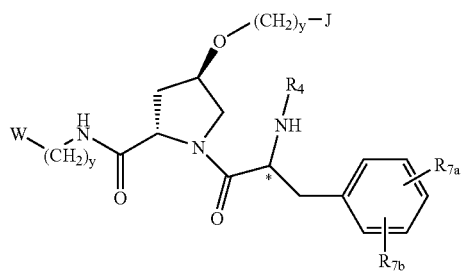
(III)

or a stereoisomer or pharmaceutically acceptable salt thereof, wherein y, J, W, Q, $R_4$, $R_5$ and $R_6$ are as defined, $R_{7a}$ and $R_{7b}$ are optional ring substituents, and when one or both are present, are the same or different and independently hydroxyl, halogen, alkyl, or aryl groups attached directly or through an ether linkage, and the carbon atom marked with an asterisk can have any stereochemical configuration.

In yet another embodiment, the invention provides a compound having the structure:

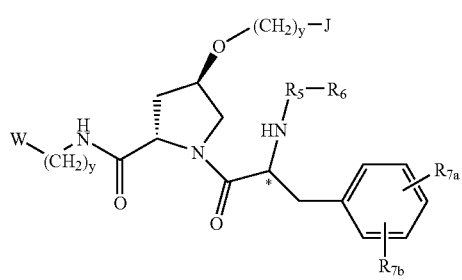
(IV)

or a stereoisomer or pharmaceutically acceptable salt thereof, wherein y, J, W, Q, $R_5$, $R_6$, $R_{7a}$ and $R_{7b}$ are as defined, and the carbon atom marked with an asterisk can have any stereochemical configuration.

The invention further provides a composition including at least one compound of any of the foregoing structures in combination with a pharmaceutically acceptable carrier.

In another embodiment the present invention provides a compound that is an agonist of a melanocortin receptor, including MC1-R, MC3-R, MC4-R, or MC5-R. The compound can also be an antagonist of a melanocortin receptor, including MC1-R, MC3-R, MC4-R, or MC5-R.

The invention further includes a method for altering a disorder or condition associated with the activity of a melanocortin receptor, comprising administering to a patient a therapeutically effective amount a compound of this invention. In one embodiment the disorder or condition is treated by administration of an MCI-R specific agent. In another embodiment the disorder or condition is melanoma or a melanin-related disorder. In yet another embodiment the disorder or condition is an inflammatory process disease.

A primary object of the present invention is provide pyrrolidine compounds, with at least three biologically-relevant pendant groups, that are specific for one or more melanocortin receptors.

Another object of the present invention is to provide pyrrolidine compounds where one pendant group consists of a single phenylalanine amino acid residue, or a derivative or homolog thereof, an optionally an amine capping group.

Another object of the present invention is to provide a method for synthesis of pyrrolidine compounds including three biologically-relevant pendant groups.

Another object of the present invention is to provide pyrrolidine compounds that are useful for the treatment of inflammatory process disease and as an anti-inflammatory agent.

Another object of the present invention is to provide a pharmaceutical compound useful for the treatment of disorders or conditions such as immunosuppressive, skin pigmentation, cardiovascular or neurogenerative diseases.

Yet another object of the present invention is to provide MCI-R specific compounds that are useful the treatment of MCI-R associated disorders.

A further object of the present invention is to provide compounds that are specific for at least one of melanocortin receptors MC1-R, MC3-R, MC4-R, or MC5-R and which are agonists or antagonists.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the compounds and combinations particularly pointed out in the appended claims.

DETAILED DESCRIPTION OF THE INVENTION

Definitions. Certain terms used in this invention, and as used in the specification and claims, are defined as follows:

The terms "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249–262, 1990; and Toniolo C: *Int J Peptide Protein Res* 35:287–300, 1990; the teachings of all of which are incorporated herein by reference.

The term "amino acid side chain moiety" used in this invention includes any side chain of any amino acid, as the term "amino acid" is defined herein, and any "derivative" of an amino acid side chain moiety, as the term "derivative" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The following abbreviations for amino acids or amino acid side chain moieties have the meanings given, it being understood that any amino acid listed may be in the L- or D-configuration:

Abu—gamma-amino butyric acid
2-Abz—2-amino benzoic acid
3-Abz—3-amino benzoic acid
4-Abz—4-amino benzoic acid
1-Ach—1-amino-cyclohexane-1-carboxylic acid
1-Acp—1-amino-cyclopropane-1-carboxylic acid
12-Ado—12-amino dodecanoic acid
Aib—alpha-aminoisobutyric acid
Aic—2-aminoindane-2-carboxylic acid
6-Ahx—6-amino hexanoic acid
Amb—4-(aminomethyl)-benzoic acid
Amc—4-(aminomethyl)-cyclohexane carboxylic acid
7'-amino-heptanoyl—$NH_2$—$(CH_2)_6CO$—
8-Aoc—8-amino octanoic acid
Arg(Tos)—$N^G$-para-tosyl-arginine
Asp(anilino)—beta-anilino-aspartic acid
Asp(3-Cl-anilino)—beta-(3-chloro-anilino)-aspartic acid
Asp(3,5-diCl-anilino)—beta-(3,5-dichloro anilino)-aspartic acid
Atc—2-aminotetralin-2-carboxylic acid
11-Aun—11-amino undecanoic acid
AVA—5-amino valeric acid
Beta-hHyp(Bzl)—Beta-(O-benzyl)-homohydroxyproline
Beta-hSer(Bzl)—Beta-(O-benzyl)-homoserine
Bip—biphenylalanine
Bzl—benzyl
Bz—benzoyl
Cha—cyclohexylalanine
Chg—cyclohexylglycine
Cmpi—4-caboxymethyl-piperazine
Dip—3,3-diphenylalanine
Disc—1,3-dihydro-2H-isoindolecarboxylic acid
Dpr(beta-Ala)—$N^{beta}$-(3-aminopropionyl)-alpha,beta-diaminopropionic acid
Et-—ethyl
GAA—epsilon-guanidino acetic acid
GBzA—4-guanidino benzoic acid
B-Gpa—3-guanidino propionic acid
GVA(Cl)— beta-chloro-epsilon-guanidino valeric acid
Heptanoyl—$CH_3$—$(CH_2)_5CO$—
hPhe—homophenylalanine
hSer—homoserine
Hyp—hydroxy proline
hHyp—homo hydroxy proline
Hyp(Bzl)—O-benzyl-hydroxyproline
Hyp(2-naphthly)—O-2' naphthyl-hydroxyproline
Hyp(Phenyl)—phenyl-hydroxyproline
Idc—indoline-2-carboxylic acid
Igl—indanylglycine
Inp—isonipecotic acid Lys(Z)—N-epsilon-benzyloxycarbonyl-lysine
Me-—methyl
Nal 1—3-(1-naphthyl)alanine
Nal 2—3-(2-naphthyl)alanine
(N-Bzl)Nal 2—N-benzyl-3-(2-naphthyl)alanine
2-Naphthylacetyl—2-naphthyl-$CH_2CO$—
(Nlys)Gly—N-(4-aminobutyl)-glycine
(N-PhEt)Nal 2—N(2-phenylethyl)-3-(2-naphthyl)alanine
OcHx—cyclohexyl ester
Phg—phenylglycine
pF-Phe—para-fluoro-phenylalanine
Phe(4-Br)—4-bromo-phenylalanine
Phe(4-$CF_3$)—4-trifluoromethyl-phenylalanine
Phe(4-Cl)—4-chloro-phenylalanine
Phe(3-Cl)—3-chloro-phenylalanine
Phe(2-Cl)—2-chloro-phenylalanine
Phe(2,4-diCl)—2,4,-dichloro-phenylalanine
Phe(2,4-diF)—2,4-difluoro-phenylalanine
Phe(3,4-diCl)—3,4,-dichloro-phenylalanine
Phe(5-Cl)—5-chloro-phenylalanine
Phe(3,4-diF)—3,4,-difluoro-phenylalanine
Phe(4-I)—4-iodo-phenylalanine
Phe(3,4-di-OMe)—3,4,-dimethoxy-phenylalanine
Phe(4-Me)—4-methyl-phenylalanine
Phe(4-OMe)—4-methoxy-phenylalanine
Phe(4-NC)—4-cyano-phenylalanine
Phe(4-$NO_2$)—4-nitro-phenylalanine
Pip—pipecolic acid
Pr—propyl
Pr-I—isopropyl
3-Pya—3-pyridylalanine
Pyr—pyroglutamic acid
Qal(2')—beta-(2-quinolyl)-alanine
Sal—3-styrylalanine
Sar—sarcosine
Ser(Bzl)—O-benzyl-serine
Ser(2-Naphthyl)—O-2-Naphthyl-serine
Ser(Phenyl)—O-2-Phenyl-serine
Ser(4-Cl-Phenyl)—O-4-Cl-Phenyl-serine
Ser(2-Cl-Phenyl)—O-2-Cl-Phenyl-serine
Ser(p-Cl-Bzl)—O-4-Cl-Benzyl-serine
Thr(Bzl)—O-Benzyl-threonine
Tic—1,2,3,4-tetrahydroisoquinoline-3-carboxylic acid
Tiq—1,2,3,4-tetrahydroisoquinoline-1-carboxylic acid
Tle—tert-butylalanine
Tpi—1,2,3,4-tetrahydronorharman-3-carboxylic acid
Tyr(Bzl)—O-benzyl-tyrosine
Tyr(2,6-DiCl-Bzl)—O-(2,6 dichloro)benzyl-tyrosine
Z—benzyloxycarbonyl Conventional amino acid residues have their conventional meaning as given in Chapter 2400 of the *Manual of Patent Examining Procedure*, $7^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

In the specification and the claims, the term "homolog" includes, without limitation, (a) a D-amino acid residue or side chain substituted for an L-amino acid residue side chain, (b) a post-translationally modified residue or side chain substituted for the residue or side chain, (c) a nonprotein or other modified amino acid residue or side chain based on another such residue or side chain, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxycarbonyl. Examples of an aryl group include phenyl, biphenyl, naphthyl, 1-naphthyl, and 2-naphthyl, derivatives thereof, and the like.

The term "aralkyl" includes a radical—$R^a R^b$ where $R^a$ is an alkylene (a bivalent alkyl) group and Rb is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl [—(C=O)—] groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

An "amine capping group" includes any terminal group attached through a terminal amine, including but not limited to any omega amino derivative, acyl group or terminal aryl or aralkyl including groups such as hexyl, hexanoyl, heptanoyl, acetyl, cinnamoyl, phenylacetyl, cyclohexylacetyl, naphthylacetyl, propylpentanoyl, benzyl, benzoyl, benzyloxycenbonyl, cinnamoyl, 12-Ado, 7'-amino heptanoyl, 6-Ahx, Amc, and 8-Aoc.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more pharmaceutically active ingredients and agents.

A variety of chemicals and compounds are employed in this invention, and the following abbreviations have the meanings given:

Boc tertiary butyloxycarbonyl
DCM dichloromethane
DIEA N,N-diisopropylethylamine
Fmoc 9-fluorenylmethoxycarbonyl
HEPES 4-(2-hydroxyethyl)1-piperazineethanesulfonic acid
NMP 1-methyl-2-pyrrolidinone
TBTU 2-(1H-Benzotriazole-1-yl)-1,1,3,3-tetramethyluronium tetrafluoroborate
TFA trifluoroacetic acid
TIS triisopropylsilane "Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound of this invention, that can interact with a melanocortin receptor and initiate a pharmacological response characteristic of the melanocortin receptor. By a melanocortin receptor "antagonist" is meant a drug or a compound, including a compound of this invention, which opposes the melanocortin receptor-associated responses normally induced by a melanocortin receptor agonist agent.

By "binding affinity" is meant the ability of a compound or drug to bind to its biological target.

In a preferred embodiment, the invention provides a compound of the general structure:

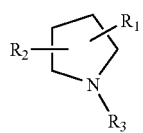

(V)

or a stereoisomer or pharmaceutically acceptable salt thereof, where $R_1$ is an amino acid side chain moiety including at least one aryl, aralkyl or heteroaryl ring, and preferably including benzyl or naphthalene;

$R_2$ is a hydrogen bonding or cationic amino acid side chain moiety; and $R_3$ is at least one amino acid residue and up to about four amino acid residues, optionally further including an amine capping group, wherein the at least one amino acid residue forming a peptide bond with the ring nitrogen includes a substituted or unsubstituted aryl or aralkyl, and preferably is a D-amino acid residue, more preferably D-Phe, optionally derivatized or substituted D-Phe.

Clinical Applications. The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist peptidomimetic compound of this invention can accordingly be used as a therapeutic chemoprevention agent for combating harmful sun or UV exposure that induces neoplastic activity in skin melanocytes.

Melanocortin receptor-specific compounds of this invention that are MC1-R specific can also be used as an anti-inflammatory agent in both acute and chronic inflammatory disease, as well as for therapy of immunosuppressive, cardiovascular and neurodegenerative diseases. Examples of inflammatory diseases include inflammation of any type or origin, such as various forms of arthritis, sclerosis, granulomatosis, psoriasis, eczema, colitis, chronic pulmonary obstruction disease and various other diseases. In part, it is thought that MC1-R specific compounds can be useful for inducing formation of the messenger element cAMP (cyclic adenosine 3',5'-monophosphate), which may be employed in treatment of inflammatory, neurodegenerative, immunosuppressive and other diseases and conditions.

In another embodiment compounds of this invention that are MC4-R agonists can be used as a therapeutic agent to modify energy metabolism and feeding behavior, including treatment of pathologic obesity and related conditions. Compounds of this invention that are MC4-R antagonists can also be used as a therapeutic agent in eating disorders, such as treatment of anorexia and cachexia, which is malnutrition and wasting due to illness. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with a maturity-onset obesity syndrome associated with hyperphagia, hyperinsulinemia and hyperglycemia.

In yet another embodiment, compounds of this invention can be used as therapeutic agents for treatment of sexual dysfunction, including treatment of both male erectile dysfunction and female sexual dysfunction. In yet another embodiment, compounds of this invention may be used as therapeutic agents for treatment of inflammation, including specifically MC1-R, MC3-R and MC5-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

The compounds may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The compounds may be administered by any systemic or partially systemic means known in the art, including but not limited to intravenous injection, subcutaneous injection, administration through mucous membranes, oral administration, dermal administration, skin patches, aerosols and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

In general, the actual quantity of compound of this invention administered to a patient will vary between fairly wide ranges depending upon the mode of administration, the formulation used, and the response desired. This may readily be determined by one of ordinary skill in the art through means such as pharmacokinetic studies, plasma half-life studies, dose escalation studies, and the like.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to induce the desired therapeutic effect.

In general, the compounds of this invention are highly active, with dose responses as low as 0.01 µg/kg, generally with optimal or peak dose responses between about 0.01 µg/kg and 25 µg/kg, depending on the specific compound and the route of administration. For example, the compound can be administered at 0.01, 0.05, 0.1, 0.5, 1, 5, 10, 50, 100, or 500 µg/kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Combination Therapy and MC1-R Specific Agents. It is also possible and contemplated to use the compounds of this invention in combination with other drugs or agents for treatment of MC1-R associated disorders. Where the metabolic pathway includes inducing cAMP production by means of MC1-R agonist compounds, any of a variety of phosphodiesterase inhibitors may be employed in combination therapy, such as inhibitors of phosphodiesterase type 1, 2, 3, 4, 7, 8, 10 or 11. Representative inhibitors include rolipram, denbutyline, 1,2-dimethylxanthine, cis-4-cyano-4-[3-(cyclopentyloxy)-4-methoxyphenyl]cyclohexane-1-carboxylic acid or the like. Such phosphodiesterase inhibitors may be administered with, prior to, or subsequent to administration of an MC1-R agonist pyrrolidine compound of the invention, and may be administered by any means known in the art.

It is also possible and contemplated to administered a compound of this invention, such as an MC1-R specific pyrrolidine compound, in association with a second drug for treatment of inflammation or inflammation-related disease, such as a steroid, a corticosteroid, a non-steroidal anti-inflammatory drug, a COX-2 inhibitor, a cytokine antagonist, and the like. Such second compound may be administered with, prior to, or subsequent to administration of an MC1-R specific pyrrolidine compound of the invention, and may be administered by any means known in the art.

Combination Therapy and Sexual Dysfunction. It is also possible and contemplated to use the compounds of this invention in combination with other drugs or agents for treatment of sexual dysfunction. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, compounds of the invention are used in combination with a therapeutically effective amount of a cyclic-GMP-specific phosphodiesterase inhibitor or an alpha-adrenergic receptor antagonist. Similarly, the compounds of this invention may be used in combination with any known mechanical aids or devices.

The present invention thus provides methods of treating sexual dysfunction, the methods comprising the step of administering to the patient having or at risk of having sexual dysfunction a therapeutically effective amount of a compound of this invention in combination with a therapeutically effective amount of a second sexual dysfunction pharmaceutical agent. The compound of this invention may be administered simultaneously with, prior to or subsequent to administration with a therapeutically effective amount of a second sexual dysfunction pharmaceutical agent. Preferably the compound of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the compound of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the compound of this invention when desired or needed by the patient.

The present invention thus provides methods of treating sexual dysfunction, the methods comprising the step of administering to a patient having or at risk of having sexual dysfunction a therapeutically effective amount of a compound of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a compound of this invention in combination with a compound that is a melanocortin receptor agonist and in combination with another compound that is useful in the treatment of sexual dysfunction.

In a preferred embodiment of combination therapy the sexual dysfunction is female sexual dysfunction. In an especially preferred embodiment of combination therapy the sexual dysfunction is erectile dysfunction. In a preferred embodiment of the foregoing methods, the melanocortin receptor agonist is an agonist of MC3-R or MC4-R, and preferably MC4-R. The agonist may be a non-selective MC3-R and MC4-R agonist.

The present invention also provides pharmaceutical compositions that comprise 1) a compound of this invention and 2) a compound that is a melanocortin receptor agonist. The present invention further provides pharmaceutical compositions that comprise 1) a compound of this invention; 2) a compound that is a melanocortin receptor agonist; and 3) a third compound useful for the treatment of sexual dysfunction. The present invention further provides pharmaceutical compositions that comprise 1) a compound of this invention and 2) a second compound useful for the treatment of sexual dysfunction.

Representative agonists of the melanocortin receptor which are a second compound useful in combination therapy are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borschart et al., Plenum Press, New York (1998); R. T. Dorr et al., Evaluation of Melanotan-II, A Superpotent Cyclic Melanotropic Peptide in a Pilot Phase-I Clinical Study. *Life Sci.* 58:1777–1784 (1996); and R. A. H. Adan, Identification of Antagonists for Melanocortin MC3, MC4, and MC5 Receptors. *Eur. J. Pharmacol.*, 269:331–337 (1994).

In one embodiment of the composition above, the agonists are melanocyte-stimulating hormones (MSH) including α-, β-, and γ-MSH and/or adrenocorticotropic hormones (ACTH).

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)-OH, as disclosed in U.S. Pat. No. 6,579,968. Alternatively, the agonist may be any agonist disclosed in any of the following patents or patent applications: U.S. Pat. Nos. 6,534,503, 6,472,398, 6,458,790, 6,410,548, 6,376,509, or 6,350,760; U.S. Published Application Nos. 2002/0137664, 2002/0004512, 2002/0143141, or US 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; dopanergic ligands; androgens; selective androgen receptor modulators (SARMs); buproprion; vasoactive intestinal peptide (VIP); neutral endopeptidase inhibitors (NEP); neuropeptide Y receptor antagonists (NPY); and bombesin receptor-3 antagonists.

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, Levitra®, Cialis®, or may be 1-[[3-(6,7-dihydro-1-methyl- 7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a compound of this invention may be used in combination with any known mechanical aids or devices.

The present invention also provides kits for the treatment of sexual dysfunction (including erectile dysfunction), the kits comprising: a first pharmaceutical composition including a compound of this invention; a second pharmaceutical composition comprising a second compound useful for the treatment of sexual dysfunction; and, a container for the first and second compositions.

Female Sexual Dysfunction. The compounds of this invention may be used to treat female sexual dysfunction as well as male sexual dysfunction. In general, the dosing schedules and doses for females are comparable to those for males.

Combination Therapy and Weight Regulation. It is also possible and contemplated to use compounds of this invention in combination with other drugs or agents for treatment of various weight and feeding-related disorders. Where the compound is an agonist or partial agonist, the compound may be employed for decreasing food intake and/or body weight in combination with any other agent or drug heretofore employed as a diet aid, or for decreasing food intake and/or body weight. Where the compound is an antagonist, the compound may be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-duhydro-1H-imidazol-2-yl)ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (−3,4-Dimethyl-2-phenylmorpholine Tartrate) commercially available from Amarin.

Suitable non-limiting serotonergic agents include sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805, which is incorporated herein by reference. Other potential inhibitors that may be employed include 5HT2c inhibitors.

Other useful compounds for reducing energy intake include, but are not limited to, certain aryl-substituted cyclobutylalkylamines as disclosed by U.S. Pat. No. 6,127,424, which is incorporated herein by reference; certain trifluoromethylthiophenylethylamine derivatives as disclosed by U.S. Pat. No. 4,148,923, which is incorporated herein by reference; certain compounds as disclosed by U.S. Pat. No. 6,207,699, which is incorporated herein by reference; certain kainite or AMPA receptor antagonists as disclosed by U.S. Pat. No. 6,191,117, which is incorporated herein by reference; certain neuropeptide receptor subtype 5 as disclosed by U.S. Pat. No. 6,140,354, which is incorporated herein by reference; and certain alpha-blocking agents as disclosed by U.S. Pat. No. 4,239,763, which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; and certain sapogenin compounds as disclosed by U.S. Pat. No. 4,680,289, which is incorporated herein by reference.

Other useful compounds include certain gamma peroxisome proliferator activated receptor (PPAR) agonists as disclosed by WO 01/30343 and U.S. Pat. No. 6,033,656, which are incorporated herein by reference and certain polypeptides such as fibroblast growth factor-10 polypeptides as disclosed by WO 01/18210, which is incorporated herein by reference.

Moreover, monoamine oxidase inhibitors that decrease energy intake or increase energy expenditure are useful with the practice of the present invention. Suitable, but non-limiting examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, useful evodiamine compounds as disclosed by U.S. Pat. No. 6,214,831, which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™. Capsules ((S)-2-formylamino-4-methyl-pentanoic acid (S)-1-[[(2S, 3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists for example certain compounds in U.S. Pat. No. 4,626,549 which is incorporated by reference herein, α-2-adrenergic and growth hormones compounds as described in U.S. Pat. Nos. 4,937,267 and 5,120,713, which are incorporated by reference herein.

Generally, a total dosage of the above-described obesity control agents or medications, when used in combination with a compound of this invention can range from 0.1 to 3,000 mg/day, preferably from about 1 to 1,000 mg/day and more preferably from about 1 to 200 mg/day in single or 2–4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megastrol acetate, adrenocorticoids such as prednisolone and dexamethasone, cyproheptidine, serotonergic drugs such as fenfluramine, neuropeptide Y, and androgen antagonists such as flutamide, nilutamide, and zanoterone.

Synthetic Methodologies. The compounds of this invention may, in large part, be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected. In a preferred conventional procedure, the compounds of this invention may be synthesized by solid-phase synthesis and purified according to methods known in the art. Any of a number of well-known procedures utilizing a variety of resins and reagents may be used to prepare the compounds of this invention.

The process for synthesizing the compounds may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired compound.

Solid phase peptide synthesis methods are well known and practiced in the art. In such a method the synthesis of compounds of the invention can be carried out by sequentially incorporating the desired amino acid residues one at a time into the growing peptide chain according to the general principles of solid phase methods. These methods are disclosed in numerous references, including, Merrifield, R. B., Solid phase synthesis (Nobel lecture). *Angew Chem* 24:799–810 (1985) and Barany et al., *The Peptides, Analysis, Synthesis and Biology*, Vol. 2, Gross, E. and Meienhofer, J., Eds. Academic Press 1–284 (1980).

In chemical syntheses, reactive side chain groups of the various amino acid residues are protected with suitable protecting groups, which prevent a chemical reaction from occurring at that site until the protecting group is removed. Usually also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); and aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, 2,2,4,6,7-pentamethyldihydrobenzofuran-5-sulfonyl (Pbf), 4-methoxy-2,3,6-trimethylbenzenesulfonyl (Mtr), and Boc.

Solid phase synthesis typically commenced from the C-terminal end of the compounds by coupling a protected Hyp(Bzl) alpha amino acid to a 1,2 diaminoethane or related 1, omega diamino homolog trityl resin. The resins are carried through repetitive cycles as necessary to add amino acids sequentially. The alpha amino Fmoc protecting groups are removed under basic conditions. Piperidine, piperazine, diethylamine, or morpholine (20–40% v/v) in DMF may be used for this purpose.

Following removal of the alpha amino protecting group, the subsequent protected amino acids are coupled stepwise in the desired order to obtain an intermediate, protected product. The activating reagents used for coupling of amino acid residues in solid phase synthesis are well known in the art. After the compound is synthesized, if desired, the orthogonally protected side chain protecting groups may be removed using methods well known in the art for further derivatization of the compound.

Reactive groups in a compound can be selectively modified, either during solid phase synthesis or after removal from the resin. For example, compounds can be modified to obtain N-terminus modifications, such as acetylation, while on resin, or may be removed from the resin by use of a cleaving reagent and then modified. Methods for N-terminus modification, such as acetylation, or C-terminus modification, such as amidation, are well known in the art. Similarly, methods for modifying side chains of amino acids are well known to those skilled in the art of peptide synthesis.

Following cleavage of compound from the solid phase following their synthesis, the compound can be purified by any number of methods, such as reverse phase high performance liquid chromatography (RP-HPLC), using a suitable column, such as a C-18 column. Other methods of separation or purification, such as methods based on the size or charge of the compound, can also be employed. Once purified, the compound can be characterized by any number of methods, such as high performance liquid chromatograph (HPLC), amino acid analysis, mass spectrometry, and the like.

While the compounds of the invention are characterized as pyrrolidine compounds, it may be seen that the compounds can also be characterized as peptides with a C-terminal hydroxyproline, further containing a C-terminal cationic center, hydrogen bond donor or hydrogen bond acceptor, and with a side chain including a substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, or substituted or unsubstituted aromatic fused heterobicyclic ring groups. Thus in one embodiment the compounds of the invention may be described by the formula:

Aaa-Bbb-Hyp($R_8$)—N($R_9$, $R_{10}$)  (VI)

or a stereoisomer or pharmaceutically acceptable salt thereof, where

Aaa is optionally present, and if present, is an amine capping group or from one to about three amino acid residues, optionally with an amine capping group;

Bbb is an amino acid residue, preferably a D-amino acid residue, with an aromatic amino acid side chain moiety, preferably including an aromatic carbocyclic ring including phenyl, substituted phenyl, naphthyl or substituted naphthyl;

$R_8$ is an amino acid side chain moiety including at least one aryl, aralkyl or heteroaryl ring, preferably benzyl or naphthalene;

$R_9$ and $R_{10}$ are each independently hydrogen or —$(CH_2)_m$—$N(R_{11}, R_{12})$;

$R_{11}$ and $R_{12}$ are each independently hydrogen, an alkyl group, an aryl group, or —C(=NH)—$NH_2$; and m is from 0 to 6.

Thus, by way of example, it may be seen that the compound of Example 9 may alternatively be designated as Ac-Nle-Ala-His-D-Phe-Hyp(Bzl)-NH($CH_2$)$_3$—$NH_2$, the compound of Example 28 as His-D-Phe-Hyp(Bzl)-$NH_2$, the compound of Example 30 as Heptanoyl-His-D-Phe-Hyp(Bzl)-NH($CH_2$)$_3$—NH—C(=NH)—$NH_2$, and so on.

The invention is further illustrated by the following non-limiting examples.

EXAMPLE 1

General Procedure for the Synthesis of Pyrrolidine Compounds 11,3-diaminopropane trityl resin (0.1 mmol, Novobiochem) was swollen in DCM for 30 minutes. The solvent was removed and N-Fmoc-O-benzyl-hydroxyproline (0.4 mmol), TBTU (0.4 mmol) and DIEA (0.6 mmol) in NMP was added to the resin. It was agitated under nitrogen for 30 minutes and washed with NMP (2 times) and DCM (2 times). The Fmoc group was removed by treatment of the resin with piperidine (20%) in NMP for 20 minutes. The resin was washed with NMP (3 times) and DCM (3 times). Subsequently, the next desired Fmoc protected amino acid was attached to the resin in the same manner as described above. The capping groups on the N-terminal on carboxylic acids were also coupled in this way. Otherwise, anhydrides were used by agitating the resin with anhydride (6 mmol) in dry pyridine for 1 hour.

After complete assembly of the compound on resin as shown in Scheme 1, the Fmoc group, if present, was removed and the resin washed with NMP (3 times), DCM (3 times), and methanol (3 times). The resin was then thoroughly dried under vacuum. The final compound was removed from the resin by treatment with TIS/TFA/DCM (2 mL; v/v/v=5/50/50) for 1 hour. The organic liquid was evaporated and the residue was purified by HPLC to give the final compound. Mass analysis was conducted to verify the molecular weight of the compound.

SCHEME 1

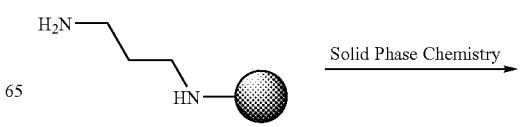

-continued

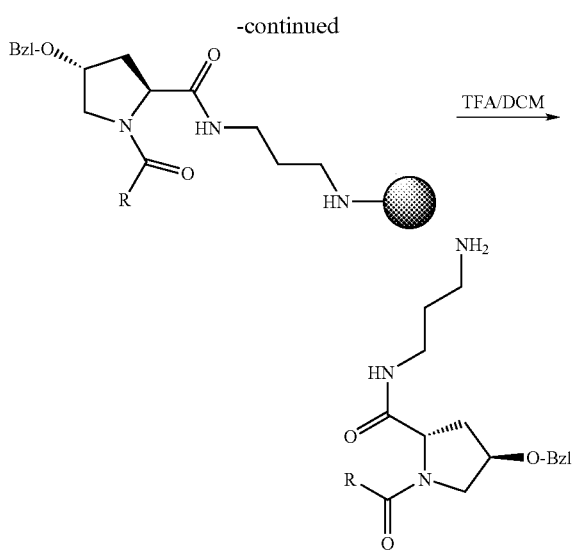

EXAMPLE 2

Competitive Inhibition Assay

A competitive inhibition binding assay was conducted using membranes prepared from hMC3-R, hMC4-R, hMC5-R, and B-16 mouse melanoma cells (containing MC1-R) using 0.4 nM $^{125}$I-NDP-α-MSH (New England Nuclear, Boston, Mass., USA) in 50 mM HEPES buffer containing 1 mM MgCl$_2$, 2 mM CaCl$_2$, and 5 mM KCl, at pH 7.2. The assay tube also contained a chosen concentration of the test compound of this invention, typically a 1 μM concentration, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 μM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in presence of test compounds were normalized with respect to 100% specific binding to determine the percent inhibition of $^{125}$I-NDP-α-MSH binding. Each assay was conducted in triplicate and the actual mean values are described.

EXAMPLE 3

EC$_{50}$ Determination in Functional Activity Assay

The Ki (nM) of certain compounds of the invention were determined. Functional evaluation of compounds at melanocortin receptors was performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM MgCl$_2$, 1 mM glutamine, 0.1% albumin and 0.6 mM 3-isobutyl-1-methyl-xanthine, a phosphodiesterase inhibitor, were plated in 96 well plates at a density of 0.5×10$^5$ cells per well. Cells were incubated with the test compounds in the presence or absence of α-MSH for 1 hour at 37° C. cAMP levels were measured by EIA (Amersham) in the cell lysates. Data analysis and EC$_{50}$ values were determined using nonlinear regression analysis with Prism Graph-Pad software.

EXAMPLE 4

Functional Status

The agonist/antagonist status with respect to MC1-4, MC4-R, and MC5-R of certain compounds of the invention was determined. Antagonistic activity was determined by measuring the inhibition of α-MSH-induced cAMP levels following exposure to the compounds as in the preceding examples.

EXAMPLE 5

Penile Erection Induction

The ability of compounds to induce penile erection (PE) in male rats was evaluated with selected compounds. Male Sprague-Dawley rats weighing 200–250 g were kept on a 12 hour on/off light cycle with food and water ad libitum. All behavioral studies were performed between 10 a.m. and 5 p.m. Groups of 4–8 rats were treated with compounds at a variety of doses via intravenous (IV) or intracerebroventricular (ICV) routes. Immediately after treatment, rats were placed into individual polystyrene cages (27 cm long, 16 cm wide, and 25 cm high) for behavioral observation. Rats were observed for 30 minutes IV or 90 minutes ICV, and the number of yawns, grooming bouts and PEs were recorded in 10-minute bins.

EXAMPLE 6

ICV Food Intake and Body Weight Change

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8–12/group) were fed powdered chow and water ad libitum. For 1 week before treatment, 24-hour food intake and body weight change was recorded to assess a baseline for the group during vehicle treatment. The rats were dosed ICV with vehicle or selected compounds (1–3 nmol). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 7

IV Food Intake and Body Weight Change

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8–12/group) were fed powdered chow and water ad libitum. For 1 week before treatment, 24-hour food intake and body weight change was recorded to assess a baseline for the group during vehicle treatment. The rats were dosed IV with vehicle or selected compounds (0.5–3 mg/kg). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 8

Determination of Mass and Nuclear Magnetic Resonance Analysis

The mass values were determined using a Waters Micro-Mass ZQ device utilizing a positive mode. Mass determinations were compared with calculated values and expressed in the form of mass weight plus one (M+1).

Proton NMR data was obtained using a Bruker 300 MHz spectrometer. The spectra were obtained after dissolving compounds in a deuteriated solvent such as chloroform, dimethyl sulfoxide, or methanol as appropriate.

EXAMPLE 9

A compound of the following structure:

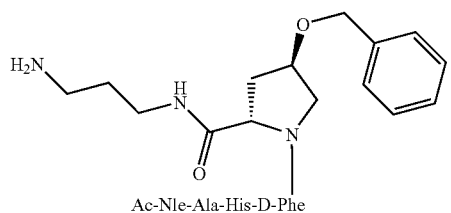

Ac-Nle-Ala-His-D-Phe was synthesized by the general method of Example 1. The molecular weight was determined to be 788.6 ESI-MS(M+1) by the method of Example 8. Competitive inhibition testing of the compound against α-MSH following the methods of Example 2 yielded the following results (average of triplicates with actual mean values described):

| Inhibition at 1 μM | | | |
|---|---|---|---|
| MC1-R | MC3-R | MC4-R | MC5-R |
| 91% | 13% | 8% | 25% |

In a cAMP assay as in Example 4 for determination of agonist/antagonist status, it was determined that the metallopeptide was an agonist of MC1-R. The Ki was determined by the method of Example 3, with the following results:

| Ki (nM) | | | |
|---|---|---|---|
| MC1-R | MC3-R | MC4-R | MC5-R |
| 10 | >1 μM | >1 μM | >1 μM |

EXAMPLE 10

A compound of the following structure:

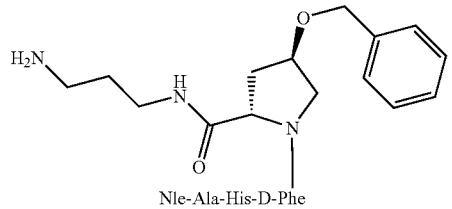

Nle-Ala-His-D-Phe was synthesized by the general method of Example 1. The molecular weight was determined to be 746.6 ESI-MS(M+1) by the method of Example 8. Competitive inhibition testing of the compound against α-MSH following the methods of Example 2 yielded the following results (average of triplicates with actual mean values described):

| Inhibition at 1 μM | | | |
|---|---|---|---|
| MC1-R | MC3-R | MC4-R | MC5-R |
| 83% | 6% | 2% | 7% |

The Ki was determined by the method of Example 3, with the following results:

| Ki (nM) | | | |
|---|---|---|---|
| MC1-R | MC3-R | MC4-R | MC5-R |
| 70 | >1 μM | >1 μM | >1 μM |

EXAMPLE 11

A compound of the following structure:

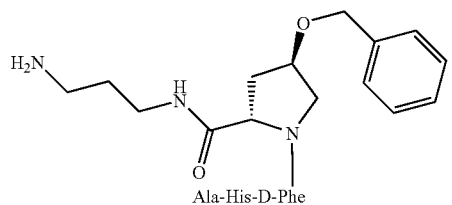

Ala-His-D-Phe was synthesized by the general method of Example 1. The molecular weight was determined to be 633.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

|       | Inhibition at 1 μM | | |
|-------|-------|-------|-------|
| MC1-R | MC3-R | MC4-R | MC5-R |
| 60%   | 0%    | 3%    | 0%    |

EXAMPLE 12

A compound of the following structure:

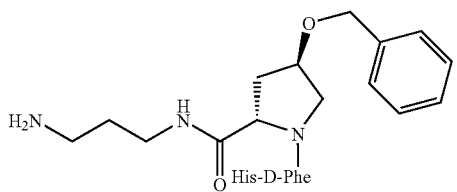

His-D-Phe was synthesized by the general method of Example 1. The molecular weight was determined to be 562.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

|       | Inhibition at 1 μM | | |
|-------|-------|-------|-------|
| MC1-R | MC3-R | MC4-R | MC5-R |
| 48%   | 0%    | 0%    | 2%    |

EXAMPLE 13

A compound of the following structure:

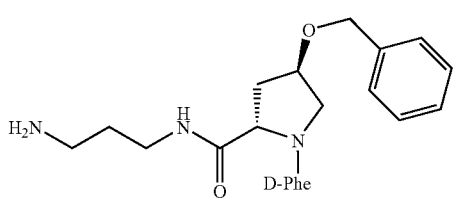

D-Phe was synthesized by the general method of Example 1. The molecular weight was determined to be 425.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

|       | Inhibition at 1 μM | | |
|-------|-------|-------|-------|
| MC1-R | MC3-R | MC4-R | MC5-R |
| 10%   | 0%    | 0%    | 0%    |

EXAMPLE 14

A compound of the following structure:

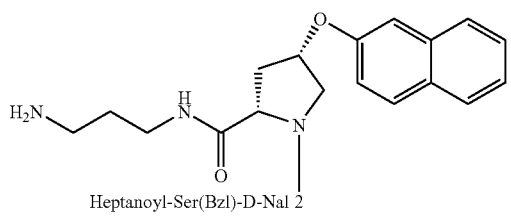

Heptanoyl-Ser(Bzl)-D-Nal 2 was synthesized by the general method of Example 1. The molecular weight was determined to be 800.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

|       | Inhibition at 1 μM | | |
|-------|-------|-------|-------|
| MC1-R | MC3-R | MC4-R | MC5-R |
| 39%   | 0%    | 0%    | 0%    |

EXAMPLE 15

A compound of the following structure:

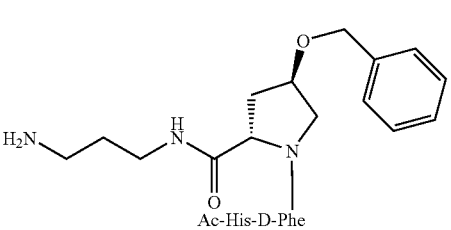

Ac-His-D-Phe was synthesized by the general method of Example 1. The molecular weight was determined to be 604.0 ESI-MS(M+1) by the method of Example 8. Competitive inhibition testing of the compound against α-MSH following the methods of Example 2 yielded the following results (average of triplicates with actual mean values described):

| Inhibition at 1 μM | | | |
|---|---|---|---|
| MC1-R | MC3-R | MC4-R | MC5-R |
| 85% | 46% | 43% | 34% |

EXAMPLE 16

A compound of the following structure:

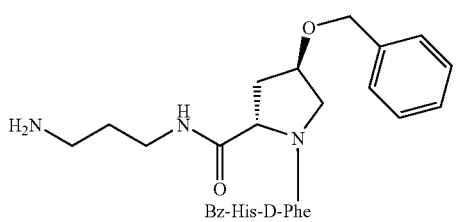

Bz-His-D-Phe was synthesized by the general method of Example 1. The molecular weight was determined to be 666.2 ESI-MS(M+1) by the method of Example 8. Competitive inhibition testing of the compound against α-MSH following the methods of Example 2 yielded the following results (average of triplicates with actual mean values described):

| Inhibition at 1 μM | | | |
|---|---|---|---|
| MC1-R | MC3-R | MC4-R | MC5-R |
| 78% | 3% | 1% | 10% |

EXAMPLE 17

A compound of the following structure:

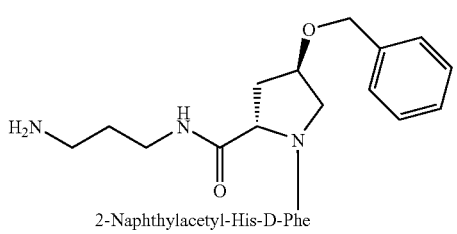

2-Naphthylacetyl-His-D-Phe was synthesized by the general method of Example 1. The molecular weight was determined to be 730.2 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 uM | | | |
|---|---|---|---|
| MC1-R | MC3-R | MC4-R | MC5-R |
| 84% | 4% | 0% | 19% |

EXAMPLE 18

A compound of the following structure:

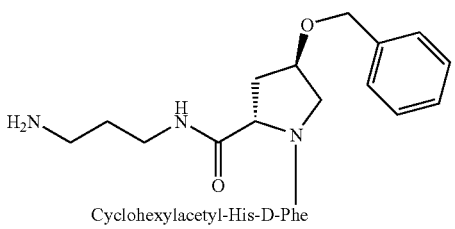

Cyclohexylacetyl-His-D-Phe was synthesized by the general method of Example 1. The molecular weight was determined to be 686.2 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 85% | 3% | 0% | 12% |

EXAMPLE 19

A compound of the following structure:

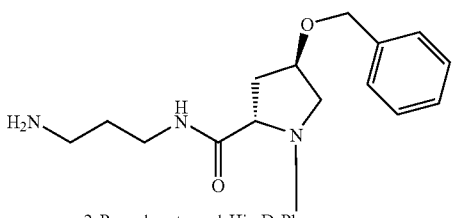

2-Propylpentanoyl-His-D-Phe was synthesized by the general method of Example 1. The molecular weight was determined to be 688.2 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 73% | 0% | 0% | 7% |

EXAMPLE 20

A compound of the following structure:

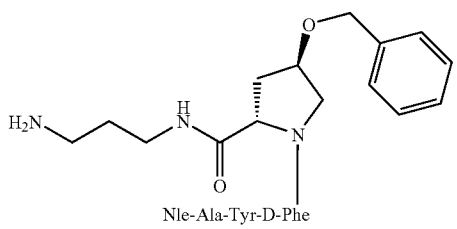

Nle-Ala-Tyr-D-Phe was synthesized by the general method Example 1. The molecular weight was determined to be 771.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 20% | 0% | 3% | 24% |

EXAMPLE 21

A compound of the following structure:

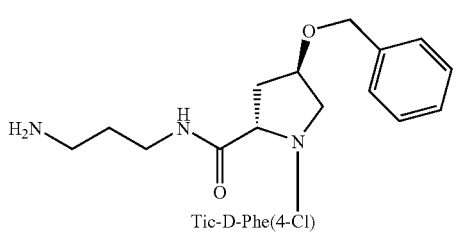

Tic-D-Phe(4-Cl)

was synthesized by the general method of Example 1. The molecular weight was determined to be 618.4 ESI-MS(M+1) by the method of Example 8. Competitive inhibition testing of the compound against α-MSH following the methods of Example 2 yielded the following results (average of triplicates with actual mean values described):

| Inhibition at 1 μM | | | |
|---|---|---|---|
| MC1-R | MC3-R | MC4-R | MC5-R |
| 40% | 6% | 29% | 48% |

The Ki was determined by the method of Example 4, with the following results:

| Ki (nM) | | | |
|---|---|---|---|
| MC1-R | MC3-R | MC4-R | MC5-R |
| >1 μM | >1 μM | >1 μM | 1146 |

EXAMPLE 22

A compound of the following structure:

D-Tic-D-Phe(4-Cl)

was synthesized by the general method of Example 1. The molecular weight was determined to be 618.0 ESI-MS(M+1) by the method of Example 8. Competitive inhibition testing of the compound against α-MSH following the methods of Example 2 yielded the following results (average of triplicates with actual mean values described):

| Inhibition at 1 μM | | | |
|---|---|---|---|
| MC1-R | MC3-R | MC4-R | MC5-R |
| 29% | 10% | 27% | 38% |

The Ki was determined by the method of Example 4, with the following results:

| Ki (nM) | | | |
|---|---|---|---|
| MC1-R | MC3-R | MC4-R | MC5-R |
| >1 μM | >1 μM | >1 μM | >1 μM |

EXAMPLE 23

A compound of the following structure:

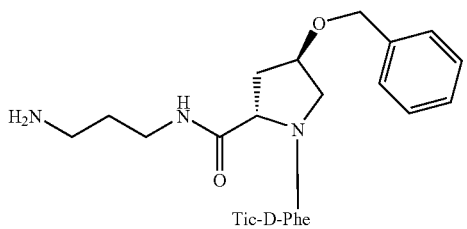

Tic-D-Phe was synthesized by the general method of Example 1. The molecular weight was determined to be 584.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 34% | 0% | 6% | 14% |

The Ki was determined by the method of Example 3, with the following results:

| Ki (nM) | | | |
|---|---|---|---|
| MC1-R | MC3-R | MC4-R | MC5-R |
| >1 µM | > 1 µM | >1 µM | > 1 µM |

EXAMPLE 24

A compound of the following structure:

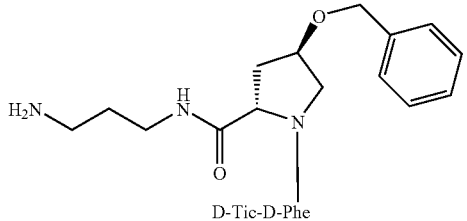

D-Tic-D-Phe was synthesized by the general method of Example 1. The molecular weight was determined to be 584.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 uM | | | |
|---|---|---|---|
| MC1-R | MC3-R | MC4-R | MC5-R |
| 17% | 0% | 5% | 0% |

The Ki was determined by the method of Example 3, with the following results:

| Ki (nM) | | | |
|---|---|---|---|
| MC1-R | MC3-R | MC4-R | MC5-R |
| >1 µM | >1 µM | >1 µM | >1 µM |

EXAMPLE 25

A compound of the following structure:

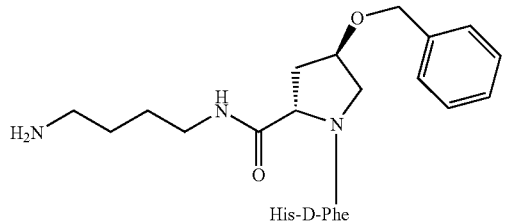

His-D-Phe was synthesized by the general method of Example 1. The molecular weight was determined to be 576.5 ESI-MS(M+1) by the method of Example 8. Competitive inhibition testing of the compound against α-MSH following the methods of Example 2 yielded the following results (average of triplicates with actual mean values described):

| Inhibition at 1 µM | | | |
|---|---|---|---|
| MC1-R | MC3-R | MC4-R | MC5-R |
| 50% | 12% | 2% | 7% |

EXAMPLE 26

A compound of the following structure:

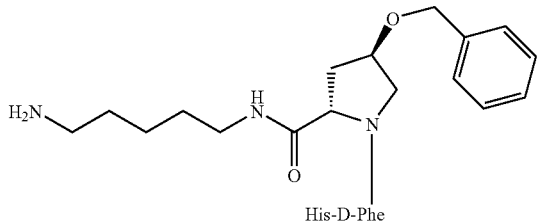

His-D-Phe was synthesized by the general method of Example 1. The molecular weight was determined to be 590.4 ESI-MS(M+

1) by the method of Example 8. Competitive inhibition testing of the compound against α-MSH following the methods of Example 2 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 42% | 0% | 1% | 7% |

EXAMPLE 27

A compound of the following structure:

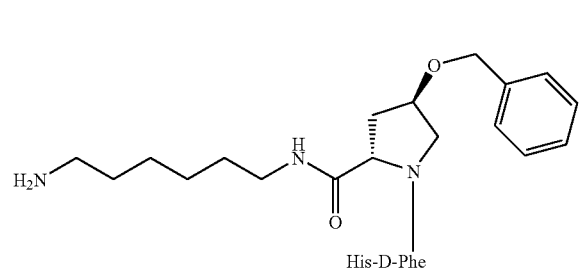

His-D-Phe was synthesized by the general method of Example 1. The molecular weight was determined to be 604.3 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 36% | 0% | 2% | 8% |

EXAMPLE 28

A compound of the following structure:

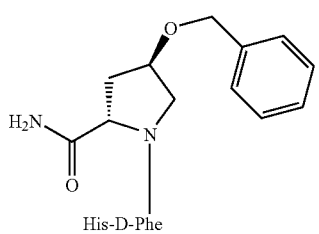

His-D-Phe was synthesized by the general method of Example 1. The molecular weight was determined to be 505.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 0% | 0% | 0% | 5% |

EXAMPLE 29

A compound of the following structure:

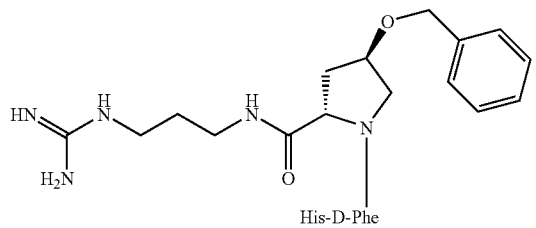

His-D-Phe was synthesized by the general method of Example 1. The molecular weight was determined to be 604.6 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 0% | 0% | 6% | 4% |

EXAMPLE 30

A compound of the following structure:

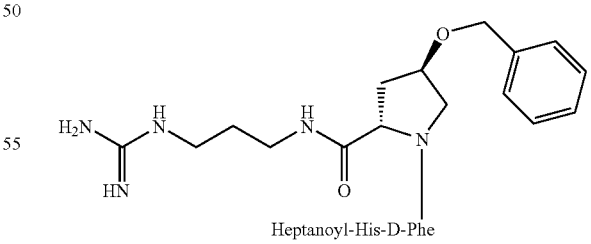

Heptanoyl-His-D-Phe was synthesized by the general method of Example 1. The molecular weight was determined to be 716.5 ESI-MS(M+1) by the method of Example 8. Competitive inhibition testing of the compound against α-MSH following the methods of Example 2 yielded the following results (average of triplicates with actual mean values described):

| Inhibition at 1 µM | | | |
|---|---|---|---|
| MC1-R | MC3-R | MC4-R | MC5-R |
| 92% | 7% | 1% | 1% |

EXAMPLE 31

A compound of the following structure:

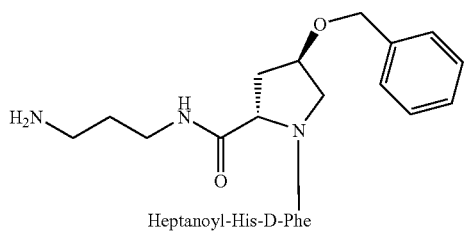

Heptanoyl-His-D-Phe was synthesized by the general method of Example 1. The molecular weight was determined to be 674.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 71% | 5% | 0% | 7% |

EXAMPLE 32

A compound of the following structure:

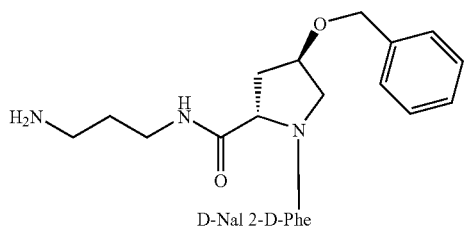

D-Nal 2-D-Phe was synthesized by the general method of Example 1. The molecular weight was determined to be 622.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 0% | 5% | 0% | 0% |

EXAMPLE 33

A compound of the following structure:

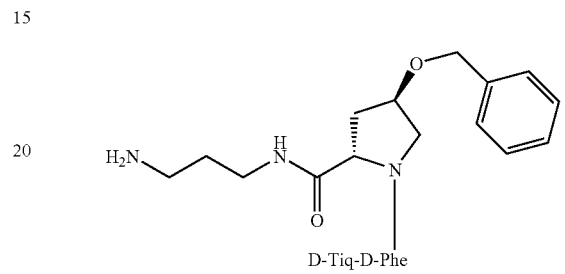

D-Tiq-D-Phe was synthesized by the general method of Example 1. The molecular weight was determined to be 584.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 0% | 14% | 1% | 0% |

EXAMPLE 34

A compound of the following structure:

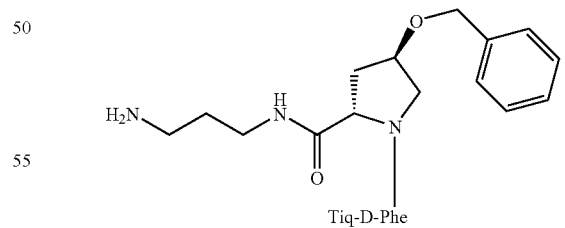

Tiq-D-Phe was synthesized by the general method of Example 1. The molecular weight was determined to be 584.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 1% | 36% | 5% | 0% |

EXAMPLE 35

A compound of the following structure:

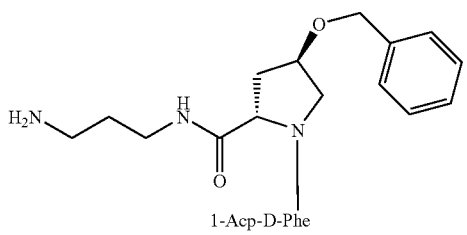

1-Acp-D-Phe was synthesized by the general method of Example 1. The molecular weight was determined to be 536.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 3% | 23% | 10% | 0% |

EXAMPLE 36

A compound of the following structure:

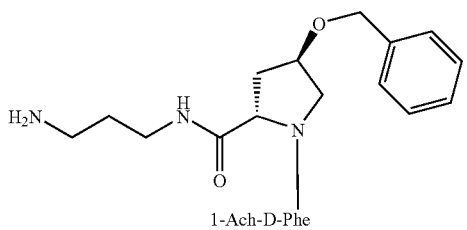

1-Ach-D-Phe was synthesized by the general method of Example 1. The molecular weight was determined to be 550.3 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 41% | 8% | 0% |

EXAMPLE 37

A compound of the following structure:

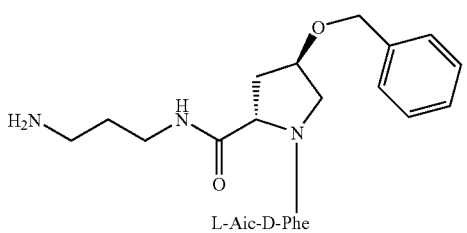

L-Aic-D-Phe was synthesized by the general method of Example 1. The molecular weight was determined to be 584.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 16% | 15% | 0% |

EXAMPLE 38

A compound of the following structure:

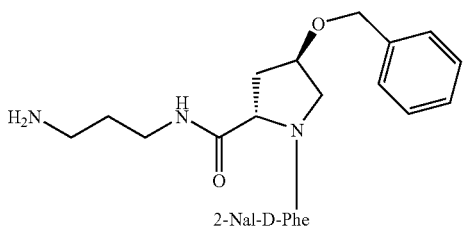

2-Nal-D-Phe was synthesized by the general method of Example 1. The molecular weight was determined to be 622.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 0% | 13% | 1% |

EXAMPLE 39

A compound of the following structure:

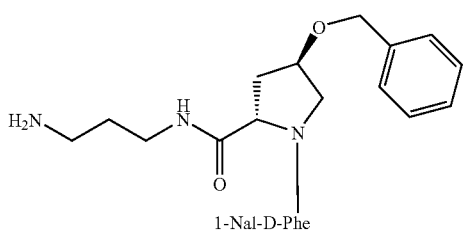

1-Nal-D-Phe was synthesized by the general method of Example 1. The molecular weight was determined to be 622.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 2% | 16% | 0% |

EXAMPLE 40

A compound of the following structure:

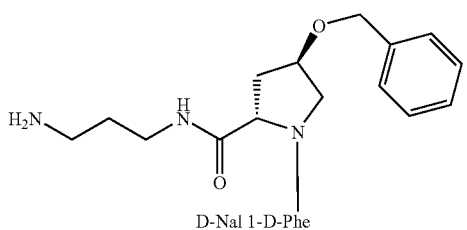

D-Nal 1-D-Phe was synthesized by the general method of Example 1. The molecular weight was determined to be 622.2 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 13% | 8% | 0% |

EXAMPLE 41

A compound of the following structure:

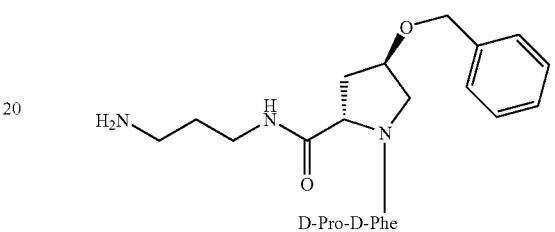

D-Pro-D-Phe was synthesized by the general method of Example 1. The molecular weight was determined to be 522.5 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 22% | 0% | 8% | 5% |

EXAMPLE 42

A compound of the following structure:

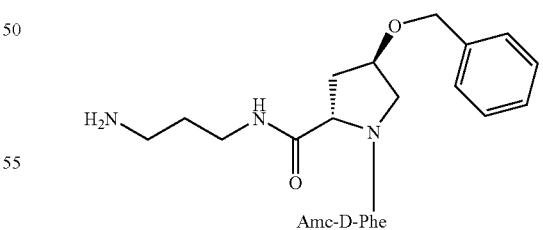

Amc-D-Phe was synthesized by the general method of Example 1. The molecular weight was determined to be 564.3 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 18% | 0% | 10% | 0% |

EXAMPLE 43

A compound of the following structure:

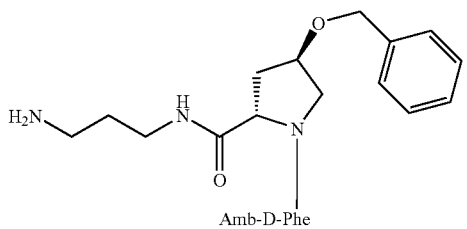

Amb-D-Phe was synthesized by the general method of Example 1. The molecular weight was determined to be 558.2 ESI-MS(M+ 1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 12% | 0% | 6% | 0% |

EXAMPLE 44

A compound of the following structure:

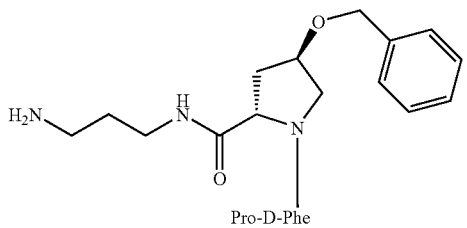

Pro-D-Phe was synthesized by the general method of Example 1. The molecular weight was determined to be 522.3 ESI-MS(M+ 1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 13% | 0% | 11% | 0% |

EXAMPLE 45

A compound of the following structure:

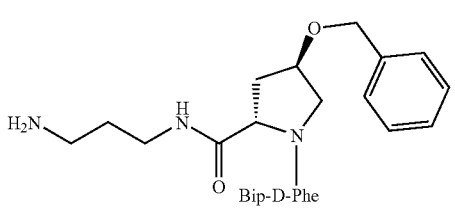

Bip-D-Phe was synthesized by the general method of Example 1. The molecular weight was determined to be 648.2 ESI-MS(M+ 1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 11% | 0% | 9% | 25% |

EXAMPLE 46

A compound of the following structure:

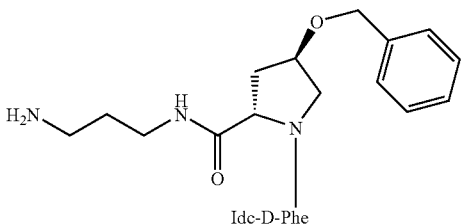

Idc-D-Phe was synthesized by the general method of Example 1. The molecular weight was determined to be 570.2 ESI-MS(M+ 1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 14% | 0% | 4% | 0% |

EXAMPLE 47

A compound of the following structure:

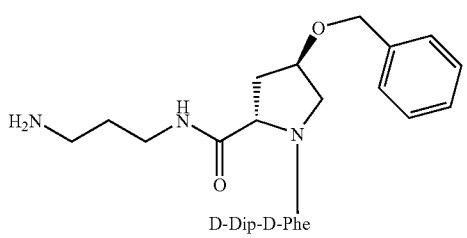

D-Dip-D-Phe was synthesized by the general method of Example 1. The molecular weight was determined to be 648.3 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 7% | 13% | 7% | 0% |

EXAMPLE 48

A compound of the following structure:

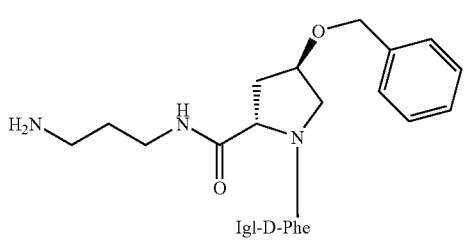

Igl-D-Phe was synthesized by the general method of Example 1. The molecular weight was determined to be 598.5 ESI-MS(M+1) by the method of Example 8. Competitive inhibition testing of the compound against α-MSH following the methods of Example 2 yielded the following results (average of triplicates with actual mean values described):

| Inhibition at 1 μM | | | |
|---|---|---|---|
| MC1-R | MC3-R | MC4-R | MC5-R |
| 10% | 21% | 15% | 2% |

EXAMPLE 49

A compound of the following structure:

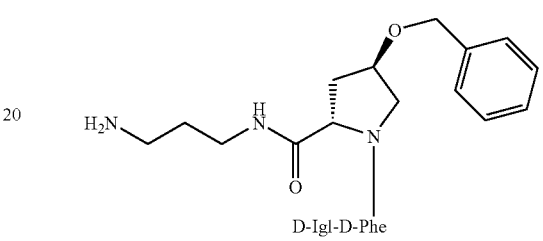

D-Igl-D-Phe was synthesized by the general method of Example 1. The molecular weight was determined to be 598.3 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 3% | 0% | 19% | 0% |

EXAMPLE 50

A compound of the following structure:

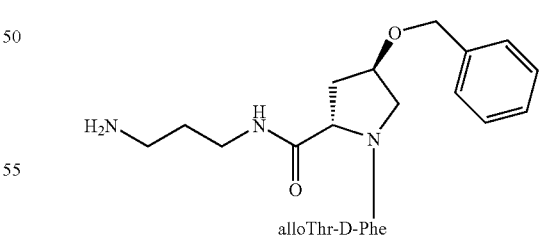

alloThr-D-Phe was synthesized by the general method of Example 1. The molecular weight was determined to be 526.3 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 µM |  |  |  |
| --- | --- | --- | --- |
| MC1-R | MC3-R | MC4-R | MC5-R |
| 18% | 0% | 8% | 8% |

EXAMPLE 51

A compound of the following structure:

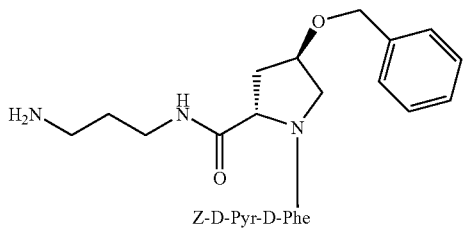

Z-D-Pyr-D-Phe was synthesized by the general method of Example 1. The molecular weight was determined to be 670.4 ESI-MS(M+1) by the method of Example 8. Competitive inhibition testing of the compound against α-MSH following the methods of Example 2 yielded the following results (average of triplicates with actual mean values described; experimental results less than 0% reported as 0%):

| Inhibition at 1 µM |  |  |  |
| --- | --- | --- | --- |
| MC1-R | MC3-R | MC4-R | MC5-R |
| 2% | 0% | 7% | 0% |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound having the structure:

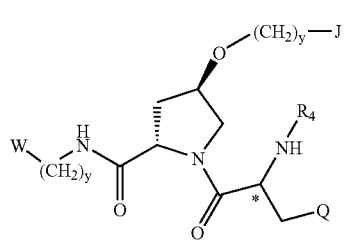

(II)

or a stereoisomer or pharmaceutically acceptable salt thereof, wherein

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings comprise 5 or 6 ring atoms;

W is a heteroatom unit with at least one cationic center, hydrogen bond donor or hydrogen bond acceptor wherein at least one atom is N;

Q is an aromatic carbocyclic ring selected from the group consisting of phenyl, substituted phenyl, naphthyl and substituted naphthyl;

$R_4$ is —$R_5$ or —$R_5$—$R_6$;

$R_5$ is from one to three amino acid residues or an amine capping group, provided that if $R_6$ is present, $R_5$ is at least one amino acid residue;

$R_6$ is H or an amine capping group; and y is at each occurrence independently from 0 to 6;

wherein the carbon atom marked with an asterisk can have any stereochemical configuration.

2. The compound of claim 1 wherein J is a substituted or unsubstituted ring structure selected from the group consisting of

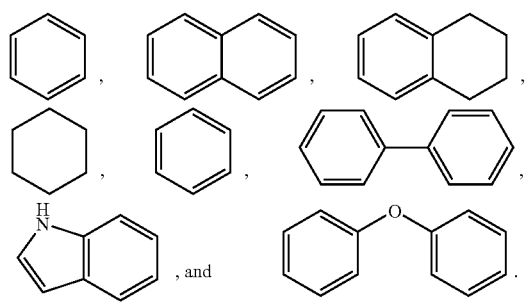

3. The compound of claim 1 wherein at least one ring comprising J is functionalized with one or more halogen, alkyl or aryl groups.

4. The compound of claim 1 wherein W is selected from the group consisting of $NH_2$, $NH(C=NH)NH_2$, —NHCOCH$_3$, —CONHCH$_3$, —NH(C=NH)NHMe, —NH(C=NH)NHEt, —NH(C=NH)NHPr, —NH(C=NH)NHPr—I, —NH(C=NH)NH$_2$NH(C=O)CH$_3$, NH(C=O)NH$_2$, —NH(C=O)NHCH$_3$,

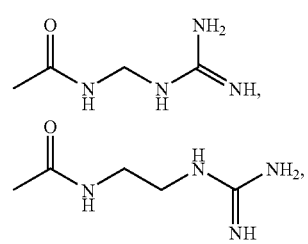

-continued

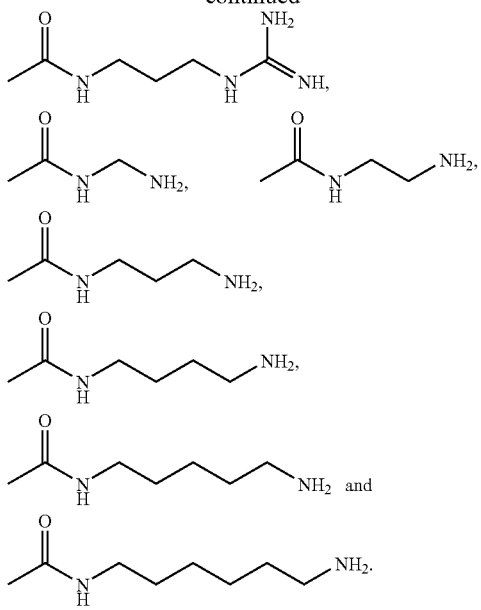

5. The compound of claim 1 where Q is

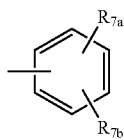

wherein $R_{7a}$ and $R_{7b}$ are optional ring substituents, and when one or both are present, are the same or different and independently hydroxyl, halogen, alkyl, or aryl groups attached directly or through an ether linkage.

6. The compound of claim 5 wherein the alkyl group is —$CH_3$ or —$OCH_3$.

7. The compound of claim 1 wherein $R_5$ or $R_6$ is an amine capping group selected from the group consisting of hexyl, hexanoyl, heptanoyl, acetyl, phenylacetyl, cyclohexylacetyl, propylpentanoyl, naphthylacetyl, cinnamoyl, benzyl, benzoyl, benzyloxycarbonyl, cinnamoyl, 12-Ado, 7'-amino heptanoyl, 6-Ahx, Amc and 8-Aoc.

8. The compound claim 1 wherein $R_4$ comprises from one to three amino acid residues selected from the group of L-amino acids consisting of Abu, 2-Abz, 3-Abz, 4-Abz, 1-Ach, Acp, Aib, Ala, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBzA, B-Gpa, GVA(Cl), His, hSer, Ser(Bzl), Tic, hHyp, Hyp(Bzl), Inp, 2-Naphthylacetyl, Nle, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl) alloThr, Thr(O-2-Cl-Phenyl), Tyr, Leu, Ile, Val and Beta-Ala.

9. The compound of claim 1 wherein $R_4$ comprises an amine capping group selected from the group consisting of hexyl, hexanoyl, heptanoyl, acetyl, phenylacetyl, cyclohexylacetyl, propylpentanoyl, naphthylacetyl, cinnamoyl, benzyl, benzoyl, benzyloxycarbonyl, cinnamoyl, 12-Ado, 7'-amino heptanoyl, 6-Ahx, Amc and 8-Aoc.

10. The compound of claim 1 having the structure:

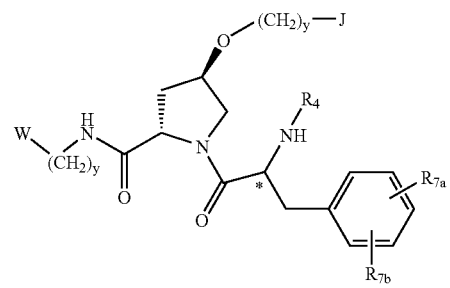

(III)

or a stereoisomer or pharmaceutically acceptable salt thereof, wherein y, J, W, $R_4$, $R_5$ and $R_6$ are as defined, $R_{7a}$ and $R_{7b}$ are optional ring substituents, and when one or both are present, are the same o different and independently hydroxyl, halogen, alkyl, or aryl groups attached directly or through an ether linkage, and the carbon atom marked with an asterisk can have any stereochemical configuration.

11. The compound of claim 10 having the structure:

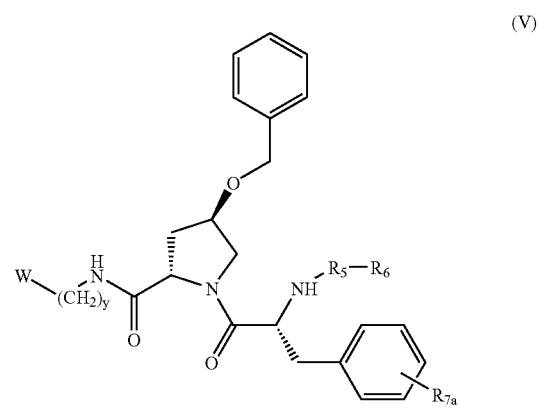

(V)

or a stereoisomer or pharmaceutically acceptable salt thereof, wherein

W is $NH_2$ or $NH(C=NH)NH_2$;

y is from 1 to 6;

$R_5$ is from one to three amino acid residues selected from the grour consisting of L- or D-isomers of Abu, 2-Abz, 3-Abz, 4-Abz, 1-Ach, Acp, Aib, Ala, Amb, Arg(Tos), Asp(anilino), Asp(3-Cl-anilino), Asp(3,5-diCl-anilino), 11-Aun, AVA, Beta-hHyp(Bzl), Bip, Cha, Chg, Cmpi, Dip, Disc, Dpr(beta-Ala), GAA, GBzA, B-Gpa, GVA(Cl), His, hSer, Ser(Bzl), Tic, hHyp, Hyp(Bzl), Inp, Nal 1, Nal 2,2-Naphthylacetyl, Nle, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Pro, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl), allo Thr, Thr(O-2-Cl-Phenyl), Tyr, Leu, Ile, Val and Beta-Ala;

$R_6$ is H or an amine capping group selected from the group consisting of acetyl, hexyl, hexanoyl, heptanoyl, acetyl, phenylacetyl, cyclohexylacetyl, prorylpentanoyl, naphthylacetyl, cinnamoyl, benzyl, benzoyl, benzyloxycarbonyl, cinnamoyl, 12-Ado, 7'-amino heptanoyl, 6-Ahx, Amc and 8-Aoc;

$R_{7a}$ is optionally present, and if present, is halogen.

12. A composition comprising a compound of any of the foregoing structures in combination with a pharmaceutically acceptable carrier.

* * * * *

UNITED STATES PATENT AND TRADEMARK OFFICE
CERTIFICATE OF CORRECTION

PATENT NO. : 7,189,755 B2
APPLICATION NO. : 10/776657
DATED : March 13, 2007
INVENTOR(S) : Sharma et al.

It is certified that error appears in the above-identified patent and that said Letters Patent is hereby corrected as shown below:

Col. 50 – Col. 51, Claim 4, delete the entire claim and replace with the following:

-- 4. The compound of claim 1 wherein W is selected from the group consisting of $NH_2$, $NH(C=NH)NH_2$, $-NHCOCH_3$, $-CONHCH_3$, $-NH(C=NH)NHMe$, $-NH(C=NH)NHEt$, $-NH(C=NH)NHPr$, $-NH(C=NH)NHPr-1$, $-NH(C=NH)NH_2$, $-NH(C=O)OCH_3$, $-NH(C=O)CH_3$, $NH(C=O)NH_2$, $-NH(C=O)NHCH_3$,

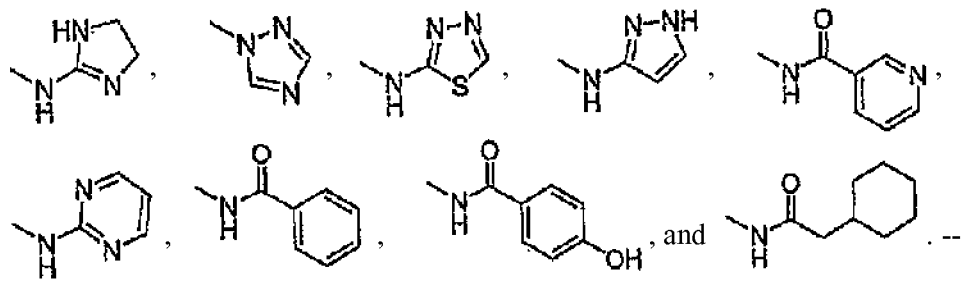

Col. 50, Claim 8, line 15, delete "4-Cl-Phenyl) allo Thr, Thr(O-2-Cl-Phenyl), Try, Leu," and replace with -- 4-Cl-Phenyl), *allo*Thr, Thr(O-2-Cl-Phenyl), Tyr, Leu, --.

Col. 52, Claim 10, line 6, delete "same o" and replace with -- same or --.

Col. 52, Claim 11, line 8, delete "grour" and replace with -- group --.

Signed and Sealed this

Fourth Day of December, 2007

JON W. DUDAS
*Director of the United States Patent and Trademark Office*